(12) United States Patent
Carl

(10) Patent No.: US 7,144,394 B2
(45) Date of Patent: *Dec. 5, 2006

(54) SELECTIVE DELIVERY OF CRYOGENIC ENERGY TO INTERVERTEBRAL DISC TISSUE AND RELATED METHODS OF INTRADISCAL HYPOTHERMIA THERAPY

(76) Inventor: Allen Carl, 308 Highgate Dr., Slingerlands, NY (US) 12159

( * ) Notice: Subject to any disclaimer, the term of this patent is extended or adjusted under 35 U.S.C. 154(b) by 126 days.

This patent is subject to a terminal disclaimer.

(21) Appl. No.: 10/653,692

(22) Filed: Sep. 2, 2003

(65) Prior Publication Data

US 2005/0149007 A1     Jul. 7, 2005

Related U.S. Application Data

(63) Continuation of application No. 10/016,266, filed on Oct. 30, 2001, now Pat. No. 6,613,044.

(60) Provisional application No. 60/243,702, filed on Oct. 30, 2000.

(51) Int. Cl.
*A61B 18/18* (2006.01)
(52) U.S. Cl. ............... 606/21; 128/898; 128/606; 128/23
(58) Field of Classification Search .......... 606/20–26; 128/898
See application file for complete search history.

(56) References Cited

U.S. PATENT DOCUMENTS

| | | | |
|---|---|---|---|
| 5,108,390 A | 4/1992 | Potocky et al. | |
| 5,417,686 A | 5/1995 | Peterson et al. | |
| 5,433,739 A | 7/1995 | Sluijter et al. | |
| 5,452,582 A | 9/1995 | Longsworth | |
| 5,531,776 A | 7/1996 | Ward et al. | |
| 5,571,147 A * | 11/1996 | Sluijter et al. | ............ 607/99 |
| 5,899,898 A | 5/1999 | Arless et al. | |
| 6,562,028 B1 | 5/2003 | Nield et al. | |

FOREIGN PATENT DOCUMENTS

RU         1727802     *   4/1992

* cited by examiner

*Primary Examiner*—Michael Peffley
(74) *Attorney, Agent, or Firm*—Pandiscio & Pandiscio

(57) ABSTRACT

The present invention relates to devices and methods for altering the tissue in and around an intervertebral disc through localized hypothermia therapy to restore function of the disc and reduce pain. Hypothermia therapy is defined as the reduction of tissue temperature to below that of the equilibrium temperature. Target therapeutic temperatures and times are varied according to the desired treatment effect. Intended effects of hypothermia of the intervertebral disc include cellular disruption leading to cell death and or structural and chemical denaturation within the anulus fibrosus, nucleus pulposus, or nerve fibers, temporary or permanent deadening of the nerves within or surrounding the disc, induction of a healing response, angiogenesis, or accelerated degeneration and/or drying of the nucleus pulposus and/or anulus fibrosus. Various effects can be achieved by reaching different temperatures for differing periods of time or by the proximity of the hypothermia therapy device to the treatment target. Accordingly, it is an object of one or more the embodiments of the invention to provide hypothermic therapy to selected locations within an intervertebral disc utilizing a flexible and guidable cryogenic device.

1 Claim, 10 Drawing Sheets

SELECTIVE DELIVERY OF CRYOGENIC ENERGY TO INTERVERTEBRAL DISC TISSUE AND RELATED METHODS OF INTRADISCAL HYPOTHERMIA THERAPY

REFERENCE TO PENDING PRIOR PATENT APPLICATION

This application is a continuation of prior U.S. patent application Ser. No. 10/016,266, now U.S. Pat. No. 6,613,044, filed Oct. 30, 2001 by Allen Carl for SELECTIVE DELIVERY OF CRYOGENIC ENERGY TO INTERVERTEBRAL DISC TISSUE AND RELATED METHODS OF INTRADISCAL HYPOTHERMIA THERAPY.

This application claims benefit to U.S. Provisional Application No. 60/243,702 filed Oct. 30, 2000, the entire teachings of this application being incorporated herein by reference.

BACKGROUND OF THE INVENTION

1. Field of the Invention

The present invention relates generally to intervertebral discs and vertebrae and methods of hypothermia therapy applied thereto to relieve pain and restore function.

2. Description of the Related Art

Low back pain afflicts more than 10 million people in the United States annually. It impacts the individual sufferer's life physically, emotionally and financially, restricting his or her activities and often leading to depression and absenteeism from work. As a nation, the United States spends more than $50 billion dollars in direct and indirect medical expenses related to back pain, making it one of the leading healthcare expenditures overall.

The intervertebral disc consists of the anulus fibrosus, nucleus pulposus, and the endplates of the superior and inferior vertebral bodies. The anulus and endplates contain the nucleus as the disc is pressurized during normal activities. The posterior anulus is thinner in cross-section than the anterior anulus and is correspondingly the site most frequently affected by injury.

Deterioration of the structure of the intervertebral disc is one of the leading causes of low back pain. The intervertebral disc is formed from a tough, outer anulus fibrosus surrounding a softer, gelatinous nucleus pulposus. The anular fibers attach securely to the endplates of the vertebral bodies superiorly and inferiorly, trapping the nucleus and creating an isobaric environment. As load is applied through the spinal column, pressure within the nucleus increases and is distributed across the vertebral endplates and anulus. These structures flex and strain until the spinal load is equilibrated by intradiscal pressure allowing the disc to act as a "shock absorber". Lack of significant vascularity in the anulus and nucleus limits their healing potential.

Small nerve endings penetrate the outer anulus. As a person ages, rents in the inner or central layers of the anulus can create focal regions of high pressure in the outer anulus that mechanically stimulates these nerve endings resulting in pain. There is also an increasing body of evidence suggesting an inflammatory response in and around nerves within the anulus and within the epidural space behind the disc induced by chemicals within the nucleus, vertebral endplates, and vertebral bodies. Passage of these chemicals through the anulus can also occur because of damage to the anulus through physical trauma, progressive aging, or degenerative disc disease. Under normal loading, portions of the nucleus or its degenerative byproducts may be forced into and through rents in the anulus, such chemicals are thought to be transported into proximity with these sensitive nerves resulting in inflammation and pain.

Therapeutic methods involving decreasing the temperature of the body or tissues thereof have a long history in medicine. Cold has been used successfully to bring about localized tissue necrosis, for cryoblation of tissue, as an anesthetic, and as a technique for inducing angiogenesis as a part of an overall healing response to the cold injury. Cryotherapy can be defined as the therapeutic use of cold and is not limited by any particular range of temperatures. Cryosurgery or cryocautery is usually more narrowly defined not merely as the use of cold in surgical applications but as the technique of exposing tissue to extreme cold in order to produce well demarcated areas of cell injury and destruction. Cryosurgical temperatures are typically below $-20°$ C. On the other hand, hypothermia therapy involves a technique of lowering body or tissues thereof below body temperature, usually between $26°$ C.–$32.5°$ C. Cryosurgery is distinguishable from the other two methods in that tissue is cut or ablated or otherwise destroyed with precision whereas cyrotherapy and hypothermia therapy techniques utilize cold or extreme cold to improve the health of tissue through stimulation. Accordingly, for purposes of this disclosure, hypothermia therapy includes cryotherapy or the therapeutic use of cold and extremely cold temperatures well below normal body temperature. Also, to the extent that related instrumentation such as hypothermia needles, cryogenic catheters, and cryoprobes (flexible or rigid) can be used to apply cryoenergy or cool tissue to a broad range of temperatures below normal body temperature, use of a specific type of instrument in a method of the invention disclosed herein does not necessarily imply a certain range of therapeutic temperatures. For instance, cryoprobes and cryocatheters may be used interchangeably according to various embodiments of the present invention.

SUMMARY OF THE INVENTION

Various embodiments of the present invention relate to devices and methods for treating the tissue in and around the intervertebral disc through localized hypothermia therapy to reduce pain or restore function in the disc and surrounding tissue. Hypothermia therapy is defined as the reduction of tissue temperature to below that of the equilibrium temperature. Target therapeutic temperature ranges from about $-272°$ C.–$37°$ C. for at least one period of up to about an hour depending upon the desired treatment effect.

According to various methods of the invention, hypothermia therapy of the intervertebral disc and adjacent vertebral bodies may be used to reduce painful pathological states of the spine. Various embodiments of the disclosed method may involve exposure of tissues including the anulus fibrosus, nucleus pulposus, and adjacent vertebral bodies including their respective nerve fibers to a range of low temperatures over a period of time. Depending on the temperatures and exposure time, this can lead to structural or chemical denaturation of tissue including selective cell death and cryoblation. The therapy may also involve temporary or permanent deadening of the nerves within or surrounding the disc. Also, hypothermia therapy may be used for the induction of a healing response, angiogenesis, or accelerated degeneration and/or drying of the nucleus pulposus and/or anulus fibrosus. Various effects can be achieved by reaching different temperatures for differing periods of time or by the proximity of the hypothermia therapy device to the treatment target. Accordingly, it is an object of one or more the embodiments of the invention to provide hypothermia therapy to selected locations within an intervertebral disc.

In one or more embodiments of the invention, the therapy may be delivered via a flexible, elongated catheter, by a flexible or rigid probe, or by a cooling element extending along at least a portion of a length of an articulated segment of a therapy delivery probe. The devices may be delivered through an open surgical approach or via percutaneous approaches to the intervertebral disc and surrounding structures.

Various embodiments of the invention may be practiced with a cryoprobe having a blunt tip or a retractable blunt or curved tip surface capable of deflecting off of the anular surface as the probe is advanced into the disc or along the surface of an anular lamella. Such a tip may also be used to deflect off of a vertebral endplate or the interior surface of a vertebral body.

The method of applying hypothermia to the disc may be accompanied by concurrent measurement of the local tissue temperature. This may be done through the use of thermocouples in the probe itself or by the use of secondary devices positioned within the tissues in or around the disc capable of temperature measurement. The region of therapy may also be monitored non-invasively through the use of ultrasound or comparable imaging technique capable of identifying the formation and extent of ice within living tissue. This technique is commonly referred to as cryomapping.

DETAILED DESCRIPTION OF THE PREFERRED EMBODIMENT

Figure 1A:
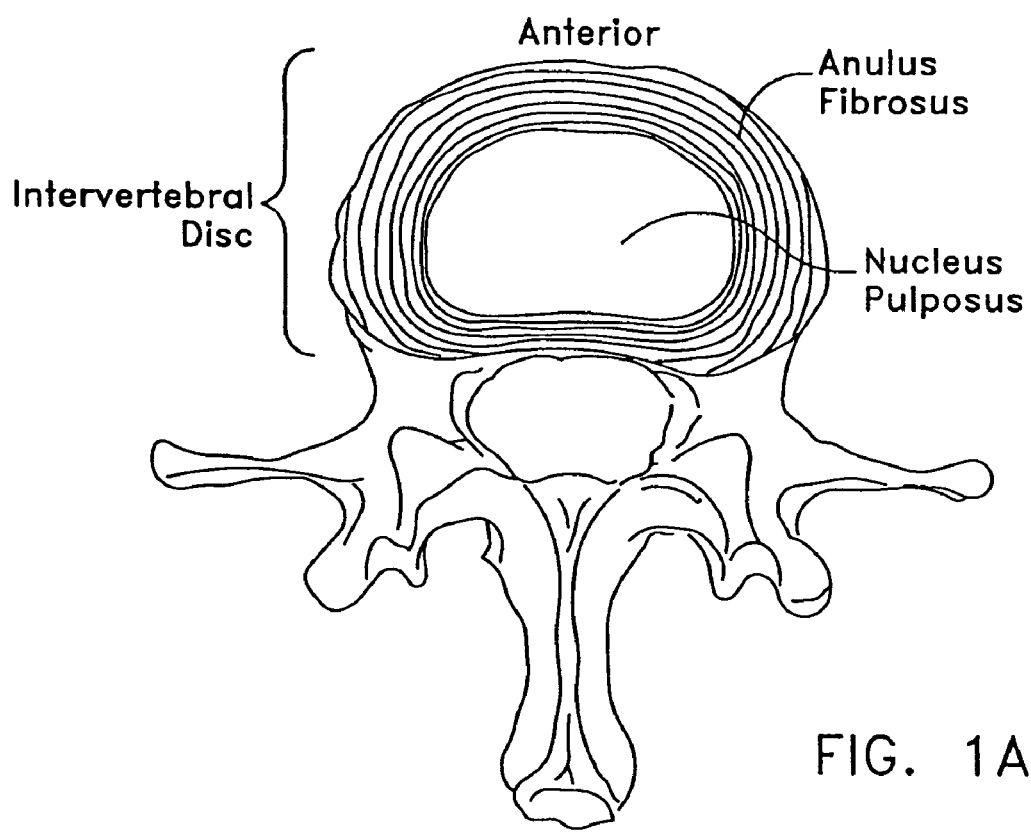
FIGS. 1A and 1B depict transverse and sagittal sections of the intervertebral disc and surrounding bony anatomy.
Figure 1B:
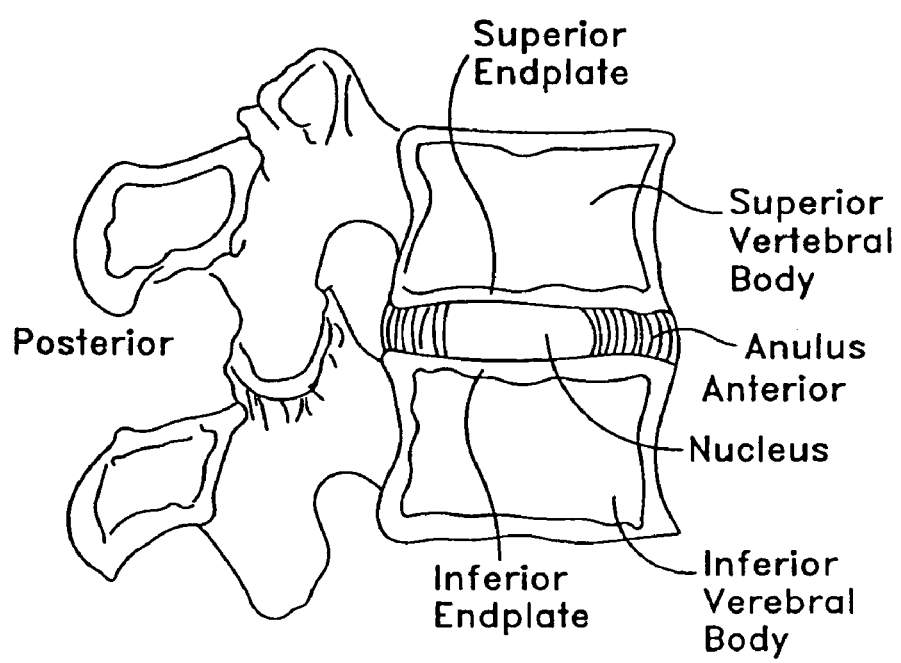

The embodiments and methods described below are given as illustrative examples of those that fall within the scope of the present invention, but are not intended to limit that scope. These devices and methods may be the sole devices and procedures performed on the intervertebral disc at the time of therapy or may accompany other procedures such as discectomy, laminectomy, fusion, decortication of the endplates, etc.

Various embodiments of the present invention relate to devices and methods for altering the tissue in and around the intervertebral disc through localized hypothermia therapy. According to several aspects of the invention, various cryogenic or hypothermic instrumentation are designed to deliver cryogenic energy within the nucleus, anulus, endplates, the epidural or dural space, or within the vertebral bodies. Hypothermia therapy and cryotherapy as used in this disclosure shall be defined as the reduction of tissue temperature to below that of the equilibrium temperature. Target therapeutic temperatures can range from about $-272°$ C.$-37°$ C. and exposure times can range from seconds to several hours depending upon the desired treatment effect. Further, the therapy may take place during one procedure or during timely spaced intervals. Multiple treatments and/or use of multiple therapeutic temperatures may be used according to various embodiments of the invention. A typical nitrous oxide cryotherapy instrument reaches temperatures around $-90°$ C. and can cauterize and destroy tissue within a few minutes of contact and may be done in cycles, e.g. for a two cycle treatment: freeze, thaw; freeze, thaw; finish. Apoptosis, or programmed cell death, can occur from the exposure of tissues to temperatures around $0°$ C. for an extended period. Here, cell death is not immediate and occurs only after a series of reactions induced by the treatment. To control pain and prevent bleeding higher temperatures above about $-20°$ C. are preferably used. For example, mild hypothermia therapy temperatures are typically in the range of about $32°$ C.$-35°$ C. These temperatures may be achieved gradually at a rate of about $0.5-1.0°$ C./hr.

Intended effects of hypothermia of the intervertebral disc and adjacent vertebral bodies according to one or more embodiments of the invention include tissue disruption leading structural denaturation, chemical denaturation, or cell death within the anulus fibrosus, nucleus pulposus, or nerve fibers, temporary deadening of the nerves within or surrounding the disc, induction of a healing response, angiogenesis, or accelerated degeneration and/or drying of the nucleus pulposus and/or anulus fibrosus. Also, it should be noted that some mechanisms of action are not fully understood involving the use of hypothermia therapy but clinical usage nonetheless proves the value of these methods in relief from back pain and restoration of function to the intervertebral disc.

According to the invention, various physiological effects may arise from mere cooling of the tissue just below body temperature to exposing the tissue to extreme cooling sufficient for cryoblation. Accordingly, inventive methods include exposure of vertebral disc and/or nuclear tissue to different temperatures for differing periods of time and by varying the proximity of the hypothermia therapy device to the treatment target. Also, other variables affecting the treatment such as the physical properties of the tissue, e.g. anular thickness and degree of herniation, depth of insertion within a tissue, and the properties of a given hypothermia device, e.g. thermal conductivity and surface area, vary widely but are readily determined by one skilled in the art through experimentation and therapeutic methods may be adjusted accordingly.

Hypothermia probes or cryogenic catheters have evolved in the art such that linear elongated lesions may be ablated using a steerable flexible tipped instrument. Such a device is described in U.S. Pat. No. 5,899,898, the teachings of which are herein incorporated by reference. Prior to such advances, only spot or regional cooling and ablation were practiced. Such probes or catheters may be sized small enough to fit through blood vessels or larger to deliver more power and present more surface area depending on the application. Also incorporated by reference is the flexible cryoprobe disclosed in U.S. Pat. No. 5,108,390. These two references also disclose external refrigeration devices for providing cryogenic energy which are suitable for use with the cryoprobes and hypothermia needles of the present invention.

The instrumentation and methods comprising several embodiments of the current invention may be utilized in a variety of surgical approaches in order to selectively deliver cryogenic energy to the tissues within and proximate to an intervertebral disc. An anterior surgical approach provides direct access to intervertebral discs but the invasiveness to the abdominal organs and blood vessels is substantial. A posterior lateral approach is less invasive but provides limited and oblique access to the disc and its interior. A transpsoas approach, i.e. across the psoas muscle is also possible. A laminectomy may be useful in increasing access to the targeted tissue but is usually not necessary if a flexible cryoprobe is used. Transpedicular and presacral or transsacral (wherein the device enters the body proximate to the sacrum and is directed cephalically toward the spine) approaches are also possible. According to a preferred embodiment of the inventive method, a hypothermia device, be it a hypothermia needle, a cryoprobe, a cryocatheter, used with or without a delivery cannula, may be inserted through or within the anulus according to any one of the surgical approach methods describe herein or as practised by surgeons. The device can be delivered through an iatrogenic hole in the anulus or through an existing defect.

The device can also be inserted within or partially through an iatrogenic hole in an adjacent vertebral body to treat the tissues within the body, especially the endplate, or within an adjacent disc.

Figure 2:
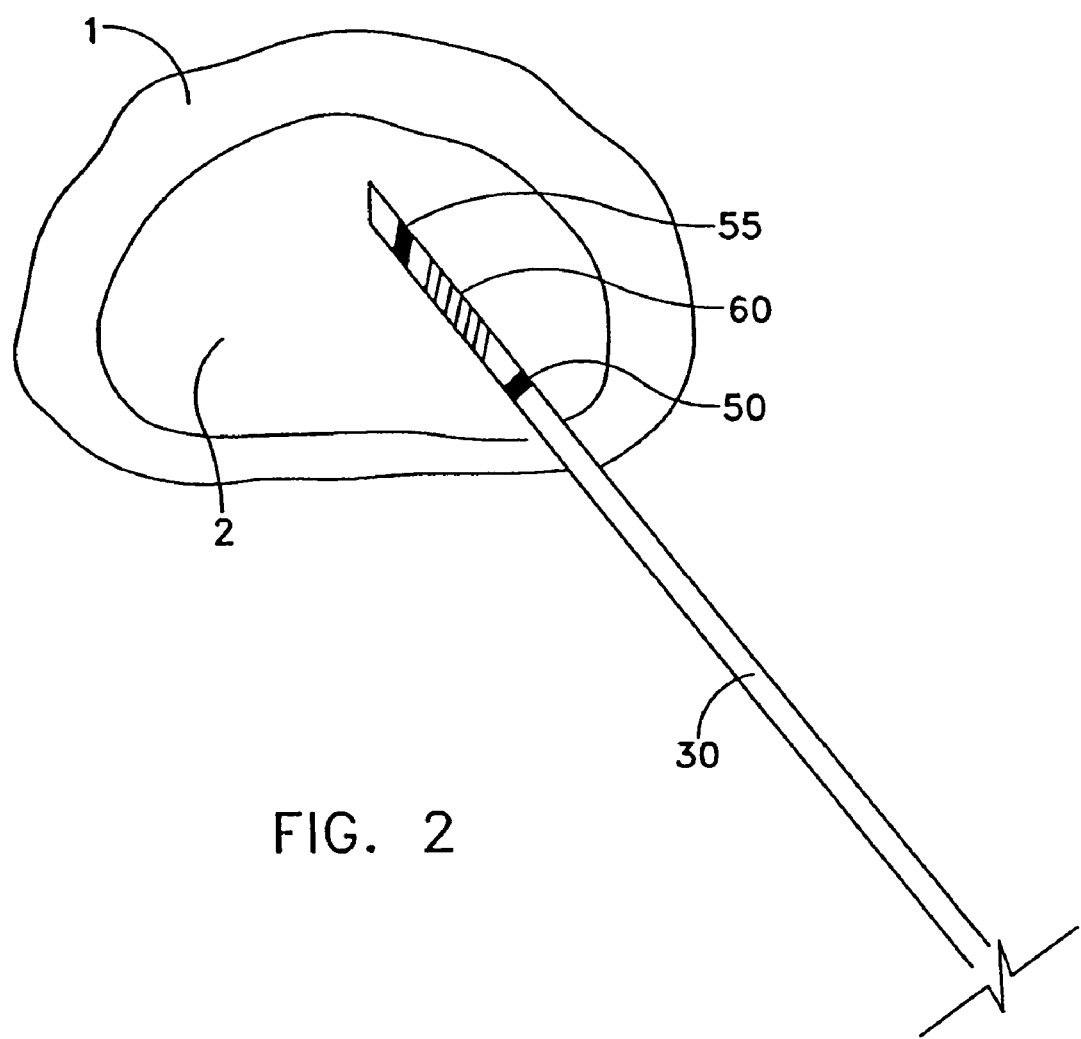
FIG. 2 is a transverse view of a disc and a cryoprobe device inserted within. The distal cutting tip is positioned within the nucleus of the disc.

FIG. 2 depicts one embodiment of the present invention and corresponding method. A transverse section of the disc including the anulus 1 and nucleus 2 with the bony anatomy removed is shown to highlight one embodiment of the present invention. The cryoprobe 30 depicted in this figure comprises a distal cutting tip 40, a proximal 50 and distal thermocouple 55, and a thermally-transmissive hypothermia region 60 in fluid or gas connection with an external refrigeration device (not shown). The thermally transmissive region 60 may be active during the entire procedure or preferably activated when advancement of the cryoprobe 30 by the surgeon causes it to be positioned adjacent to or within the targeted tissue. According to one preferred method, the cryoprobe is inserted into the nucleus through the posterior lateral anulus. Once positioned in the desired treatment site, a coolant means 70 such as refrigerated liquid, an expanding gas, or a vaporizing liquid is driven toward the thermal-transmissive region 60 of the cryoprobe 30 through interior lumens within the cryoprobe 30. Exemplary liquids comprising the coolant means 70 include HCF's, CFC's, chlorodifluoromethane, polydimethylsiloxane, ethyl alcohol, liquid nitrogen, and pentafluoroethane. Exemplary gasses comprising the coolant means 70 include nitrous oxide and carbon dioxide. Also, in addition to the circulation of cryogenic fluids from a reservoir to the thermally transmissive hypothermia region 60 of the device, the region 60 itself can be designed to be a site of a controlled endothermic reaction wherein the resultant cooling is transferred through its thermally transmissive surface to the target tissue.

Decreases in tissue temperature surrounding the cryoprobe 30 can be measured by the proximal and distal thermocouples. Thermocouples 50, 55 may be positioned proximate critical treatment landmarks to minimize spread of the therapy to non-target regions. The treatment temperature detected at the thermocouples 50, 55 may be controlled through a feedback loop (not shown). This control may be used to generate a desired time and temperature profile that may be advantageous in achieving a desired therapeutic affect. Such feedback may also help the user know when a desired temperature has been achieved. Other cryoprobes with thermocouples may be positioned in various locations to afford greater information about the temperature within and surrounding the disc and increase treatment efficiency.

The specific embodiment of the cryoprobe 30 depicted in FIG. 2 is given for illustrative purposes and is not intended to limit the scope of the present invention. The cryoprobe 30 may have only one or a multitude of thermocouples positioned at various locations along the instruments length and/or within the thermally transmissive hypothermia region 60. The thermocouples are only one of a number of possible temperature sensing devices that include, but are not limited to thermistors. Multiple thermocouples or thermistors may be used at strategic locations along the probe's 30 length. The hypothermia region 60 may be located over a contiguous length of cryoprobe 30 as shown or may be in a multitude of locations. The hypothermia region 60 may surround the circumference of the needle or may be along only one side. Also, surfaces of the cryoprobe 30 that do not contain thermally transmissive hypothermia regions 60 can be insulated so as to not conduct or absorb heat. Such an embodiment is preferable since it affords greater control of the tissues affected by the treatment. For example, the probe 30 may be thermally insulated on all but a single face or side such that when hypothermia therapy applied to a targeted area of a lamella in the posterior anulus, medial tissue towards the center of the disc such as inner lamella and the nucleus pulposus are not exposed to excess cooling.

Multiple cryoprobes may be used during a single procedure to help shape or reach the region of tissue to be treated. Other devices, such as trocars, wires or cannulae may be used to help gain access to the disc to allow insertion of the needle. In this case, the cutting tip 40 depicted in the embodiment of FIG. 2 is not necessary and may be replaced by a blunt dissection tip 45. Moreover, for certain applications, a blunt tip 45 may be preferable for deflection off of the surface of the interior of the disc, i.e. the walls of the anulus and the endplates, as the device is advanced.

Figure 3:
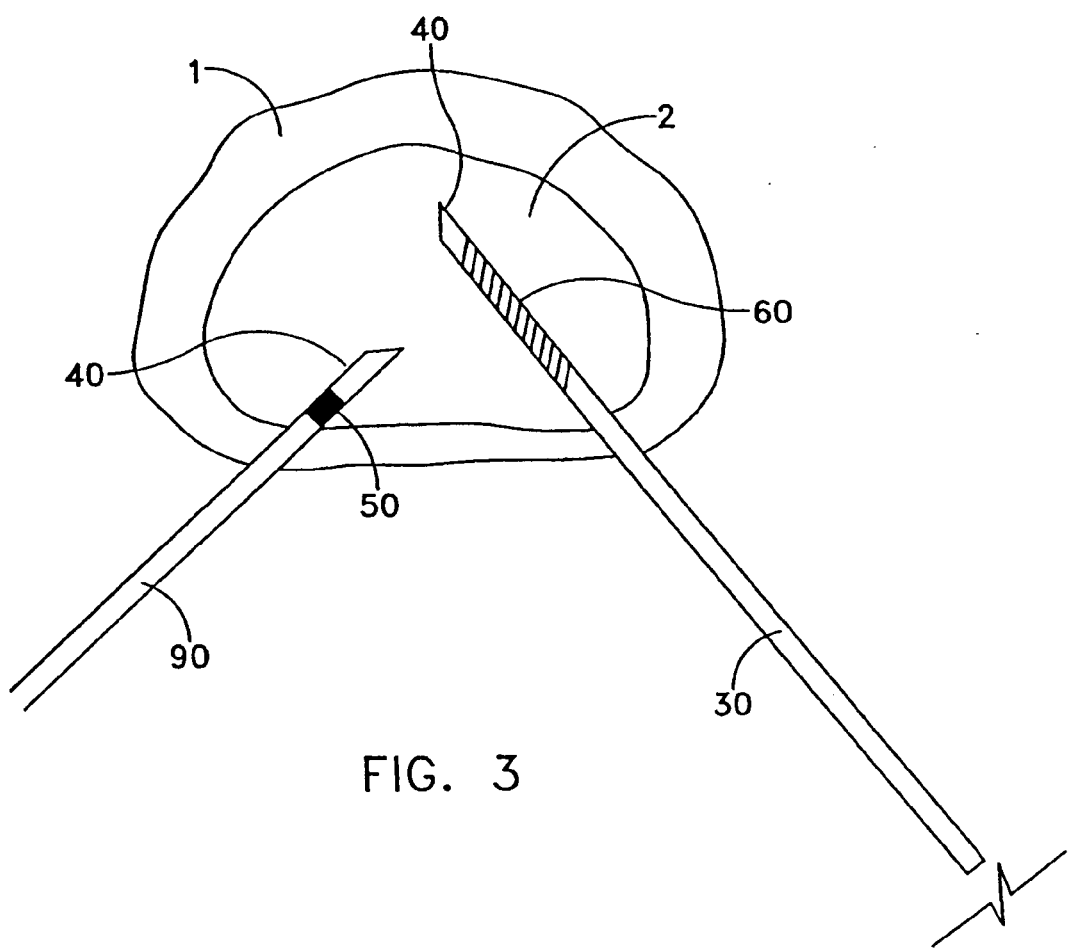
FIG. 3 is a transverse view of a disc and depicts the use of a separate temperature-sensing probe as part of a method of performing hypothermia therapy on the intervertebral disc.

FIG. 3 shows another embodiment of the cryoprobe 30 being used in combination with a separate temperature-monitoring probe 90. The temperature probe 90 is depicted with a cutting tip 40 and a thermocouple 50 and has been inserted from the contra-lateral side of the anulus into the nucleus. This probe may be positioned within or at the boundary of the targeted tissue to monitor tissue temperatures during therapy. This temperature information may be used as part of a feedback loop as discussed above.

Figure 4:
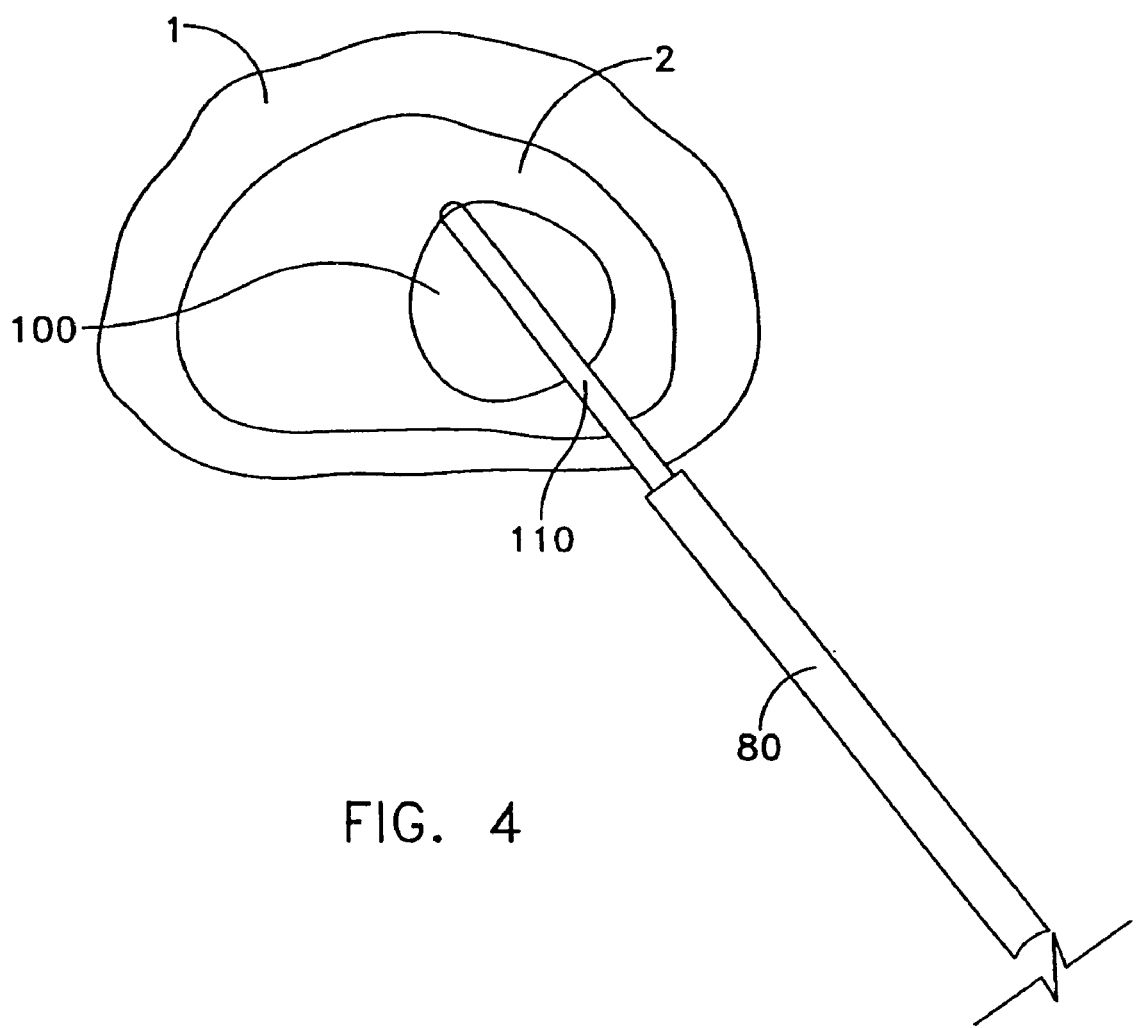
FIG. 4 is a transverse view of a disc and depicts the use of an expandable hypothermia balloon as part of the method of the present invention.

FIG. 4 depicts an expandable thermally transmissive hypothermia region or balloon 100 on the distal end of a hypothermia catheter 110. The hypothermia balloon 100 is inflated with a low temperature gas or fluid once positioned within the desired target tissues. If a fluid is employed, it should have a freezing temperature below the desired therapeutic temperature. Such fluids include, but are not limited to, alcohol or saline with a high salt content. The balloon may be in fluid connection with any of a variety of suitable refrigeration devices through interior lumens of the hypothermia catheter. The balloon 100 may be shaped or reinforced to preferentially expand in desired directions such as parallel to the vertebral endplates. The hypothermia catheter 110 is depicted with a proximal thermocouple 50 to aid in achieving therapy at the desired treatment temperature. The balloon 100 is shown within the nucleus or nuclear space, but may also be within the anulus or within a vertebral body surrounding the disc.

The catheter 110 may be wholly or partially flexible along all or a portion of its length. It may be inserted through the lumen of cannula 80 or advanced without support through an existing incision or defect in the anulus from any of the surgical approaches described above.

Figure 5:
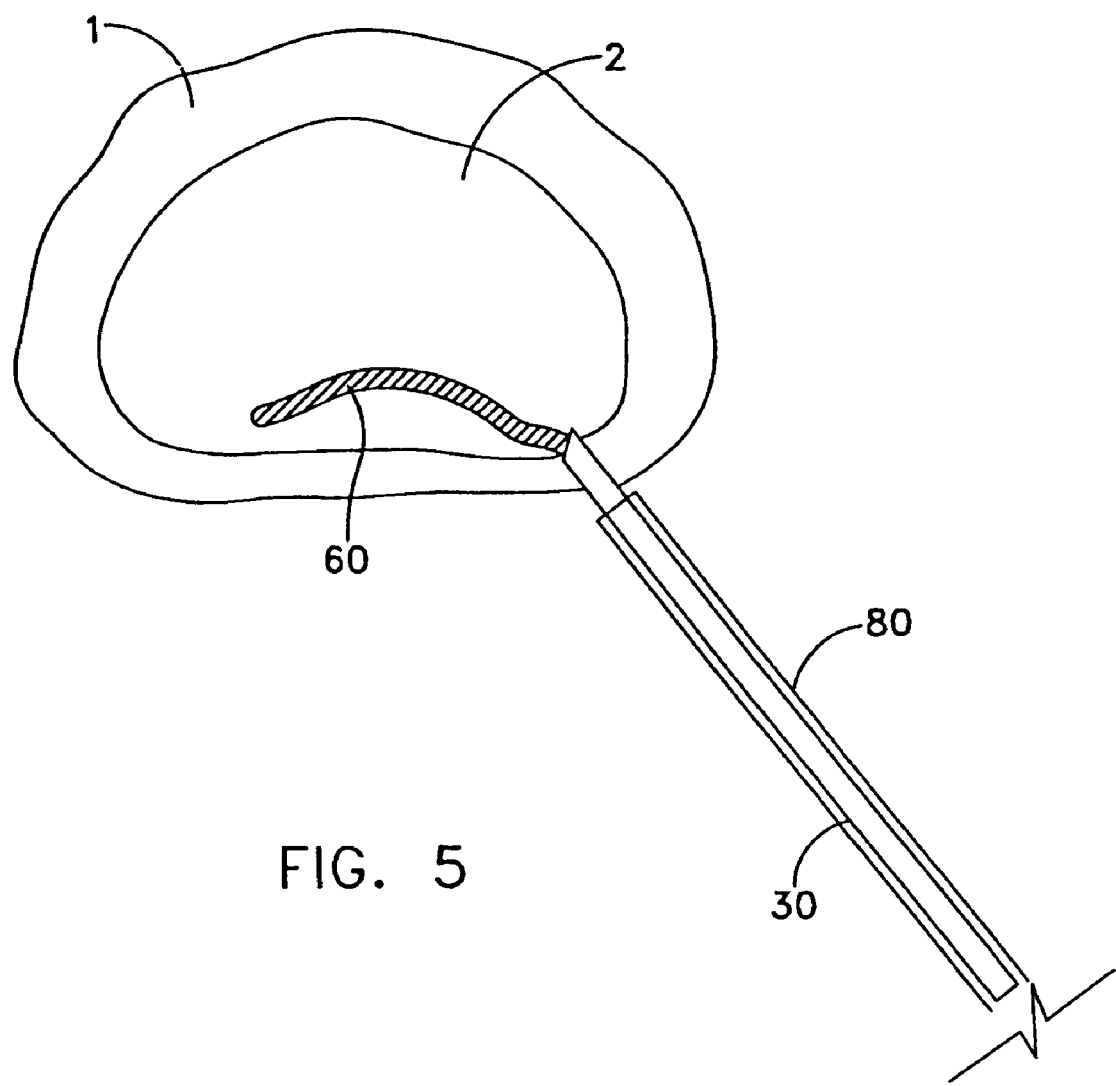
FIG. 5 is a transverse view of a disc and depicts a cryoprobe with an articulated or flexible region towards the distal end. The flexible region is positioned toward the posterior aspect of the disc to treat the posterior anulus.

FIG. 5 depicts the cryoprobe 30 and a method for selectively treating tissue along the lateral and posterior anulus. This position is also effective for treating tissues within the posterior anulus i.e., intra-anularly or between lamella of the anulus. In this embodiment, the cryoprobe 30 of the present invention is flexible and articulated. It should be understood that no limitation is implied by the use of the word "cryoprobe". Other instruments, including a cryocatheter, used according to these methods could be designed and used in the identical manner. The probe 30 may be wholly or partially flexible or rigid along all or a portion of its length. Also, the probe 30 may exhibit different stiffnesses in different planes such that travel in a single plane is encouraged and travel or flex in planes orthogonal to that plane are not possible. The probe 30 can be biased or preshaped to form a curve of similar radius of the subject intervertebral disc. Such curvatures can be advantageous in directing the probe along the surface of an anular lamella and toward target tissues.

The probe 30 may be inserted through a straight cannula 80 into the disc and then advanced out of the cannula 80 to take on its pre-formed shape. Alternatively, the probe can be articulated to allow control of its shape and orientation by the user from outside of the disc through a system of guide wires and joints running along the length of the probe 30. In addition, the probe 30 may be passed through the interior of a curved, bent or articulated delivery cannula 80 and delivered along the surface of the anulus. The cannula may be selectively insulated along all or a portion of its length to help shape the treated region of tissue.

Figure 6:
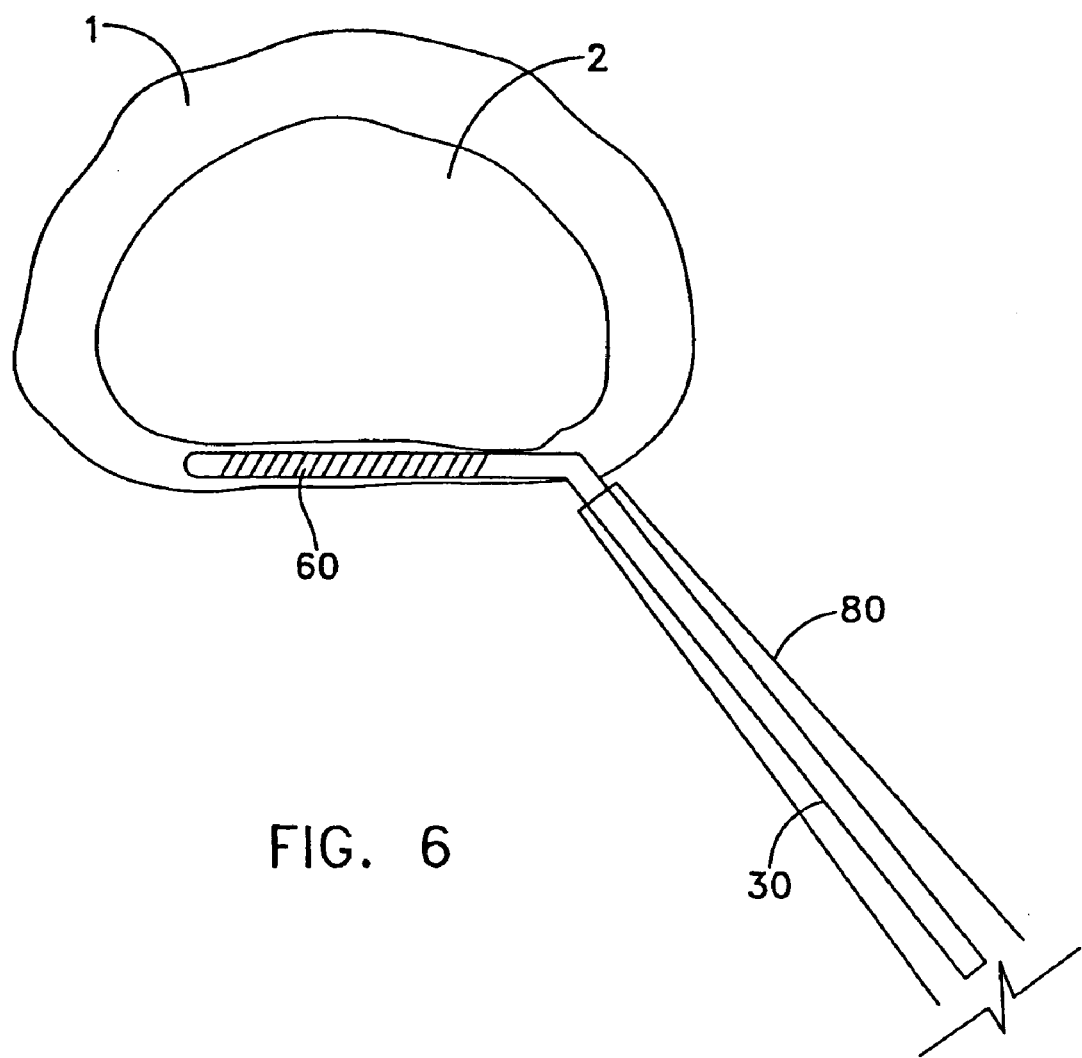
FIG. 6 is transverse view of a disc and depicts a cryoprobe with an articulated or flexible region and is positioned within the layers of the posterior anulus.
Figure 7:
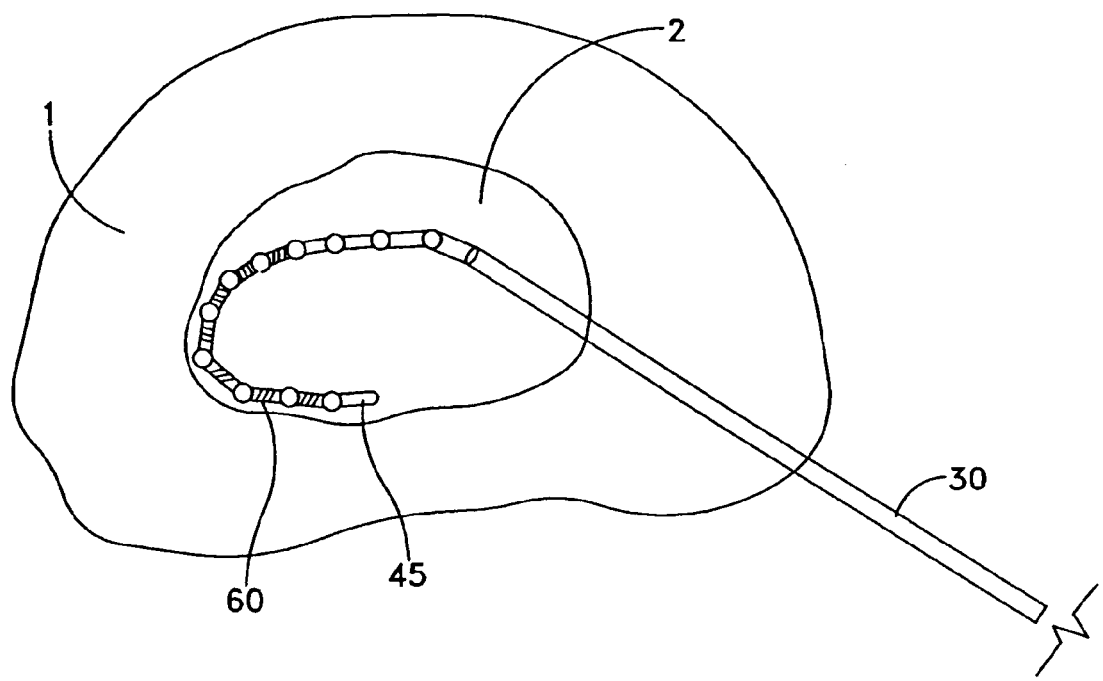
FIG. 7 is a transverse view of a disc and depicts a method of advancing a blunt tipped cryoprobe along the interior of the anulus enabling the thermally transmissive region to be positioned adjacent the tissue of the posterior anulus.

FIG. 6 depicts an alternative method of treating tissues within the posterior anulus of the disc. The flexible cryoprobe 30 has been advanced between lamellae of the anulus along the posterior anulus. This allows for precise localization of the intended hypothermia treatment to this tissue. FIG. 7 depicts another method of treating tissues within the posterior anulus of the disc. The delivery cannula 80 is inserted through an iatrogenic hole or pathological hole in the posterio-lateral anulus. The probe 30 is then advanced out of the cannula 80 through the nucleus pulposus and then deflected off of the anulus and further advanced along the anular surface until it reaches the target location along the opposites side of the posterior anulus. According to this method, the tissue of the anterior anulus may also be treated simply by not advancing the probe 30 within the disc so far as to cause it to arc around or deflect off of the anular surface and activating the thermally transmissive hypothermia region 60 located near the distal end of the probe 30 when it contacts anular tissue along the anterior anulus. In this application, a blunt or curved tip 45 is useful for deflecting of the anular surface. Also, a slight curvature or bias of the probe aids in the control and predictability of the path traveled by the probe.

Figure 8:
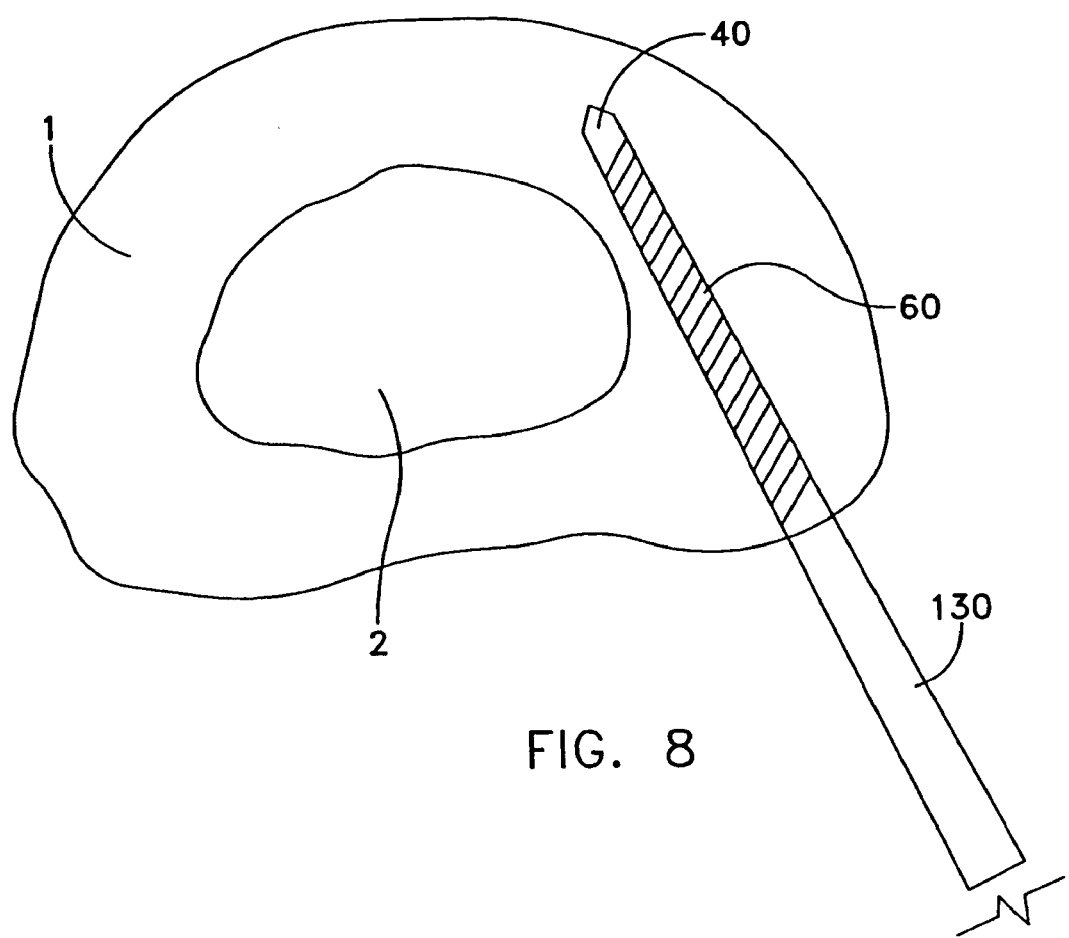
FIG. 8 is a transverse view of disc and depicts a hypothermia needle inserted within the posterior anulus from a transpsoas approach.
Figure 9:
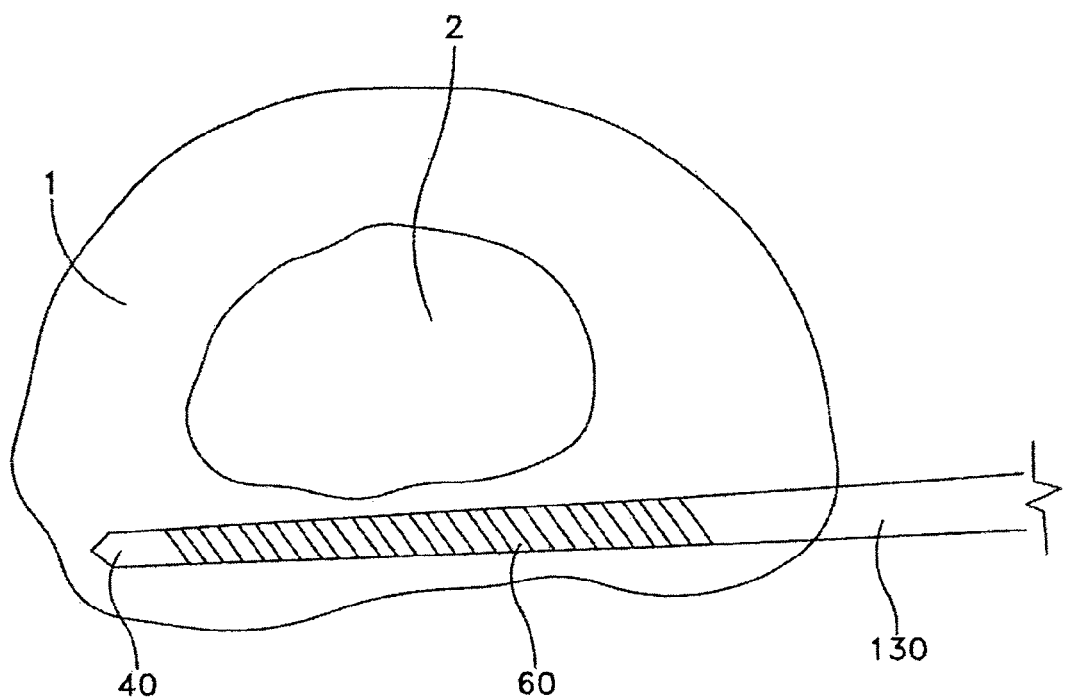
FIG. 9 is a transverse view of the disc and depicts a hypothermia needle inserted within the lateral anulus from a posterio-lateral approach.

Instrumentation smaller and less invasive than standard cryoprobes, such as hypothermia needles (which utilize the same technology as the cryoprobes in transferring cryogenic energy but are generally stiffer and of a smaller diameter) may be used and inserted at various points and depths within the anulus. This method is shown in FIG. 8 and depicts a hypothermia needle 130 treating tissue in the posterior anulus from a transpsoas approach. FIG. 9 is a transverse view of the disc and depicts the hypothermia needle 130 treating tissue within the lateral and anterior anulus from a posterio-lateral approach.

Figure 10:
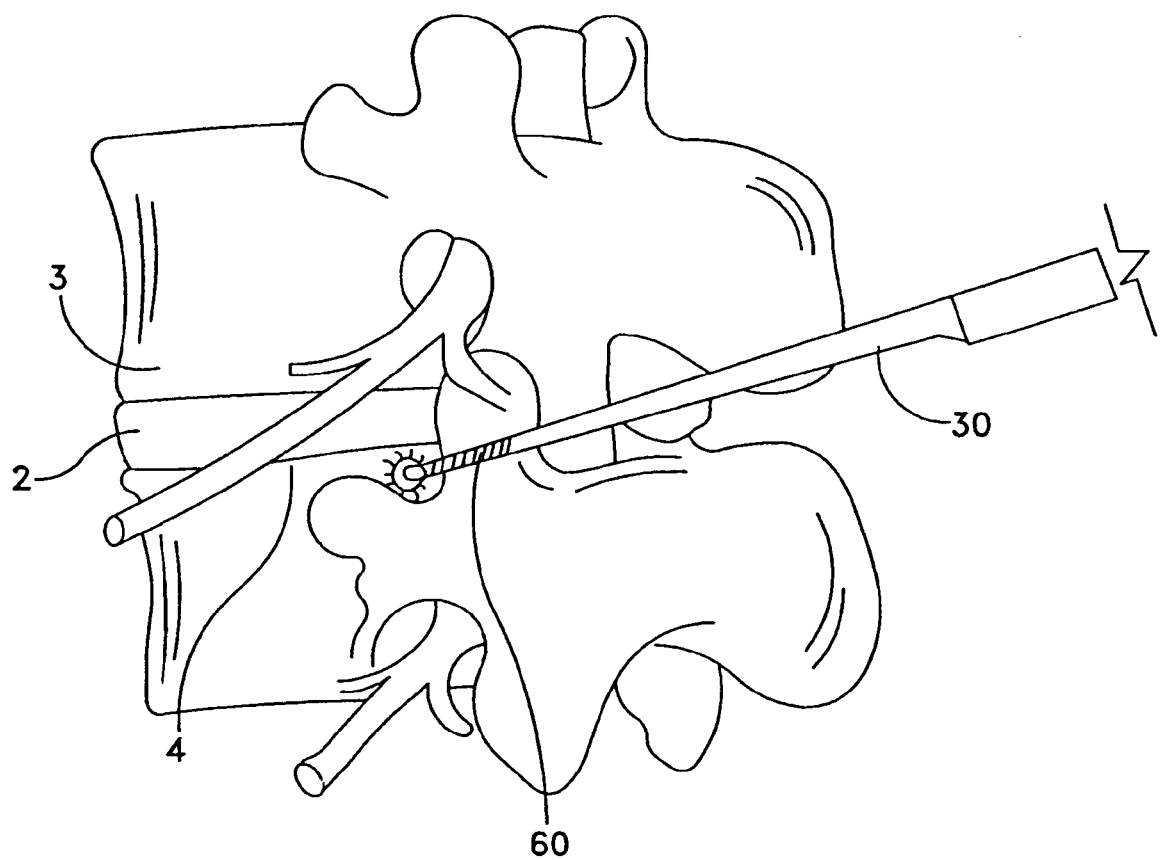
FIG. 10 is a side view of the cryoprobe inserted within an inferior vertebral body.

FIG. 10 depicts a method wherein a hypothermia device is used to treat a vertebral body and especially its endplate which defines the surface in direct communication with the adjacent disc. Vertebral endplates contain sensitive nerves and are often a significant source of back pain. Here an iatrogenic access hole is drilled into the bone to allow insertion of the cryoprobe 30 within. Alternatively, the cryoprobe 30 may simply contact the bone surface. Hypothermia therapy applied to vertebral bodies is particularly advantageous in reducing pain, stimulating a healing response in the marrow and bone tissue, and destroying tumors and growths. Alternatively, the endplates may be treated from within the disc by advancing the cryoprobe into the nucleus and presenting the thermally transmissive region 60 vertically such that it is adjacent to the targeted endplate tissue.

In addition to tactile feedback from the device it may be preferable to monitor the percutaneous travel of the device in situ. MRI, ultrasound, and other imaging techniques may be utilized to monitor the location of the hypothermia therapy device and hypothermic zone itself as it expands. This tracking of the cooling zone is known as cryomapping and is well known in the art. If real time viewing is employed, this method can be used to monitor the actual physiological progress rather than relying on measurements of exposure time and approximations of various tissue chemical and physical properties and corresponding responses to hypothermia therapy.

The foregoing description of preferred embodiments of the invention has been presented for purposes of illustration and description. It is not intended to be exhaustive or to limit the invention to the precise forms disclosed. Many modifications and variations will be apparent to practitioners skilled in the art. It is intended that the scope of the invention be defined by the following claims and their equivalents.

What is claimed is:

1. A method of delivering cryogenic energy for the treatment of selected tissue within a vertebral body comprising:
   providing a cryoprobe having a distal tip and a thermally transmissive region located proximate to said distal tip;
   inserting the cryoprobe into the patient so that the thermally transmissive region is located proximate to an endplate of the vertebral body;
   activating said thermally transmissive region; and
   delivering cryogenic energy to the endplate of the vertebral body for one or more time periods in the range of 1 minute to 60 minutes so as to treat the patient.

* * * * *